United States Patent
Zhang et al.

(10) Patent No.: US 8,105,837 B2
(45) Date of Patent: Jan. 31, 2012

(54) METHOD FOR AUTOMATIC ASSAY OF ANIONIC DETERGENTS IN SEAWATER

(75) Inventors: Xinshen Zhang, Chengdu (CN); Xiaoping Jiang, Chengdu (CN)

(73) Assignee: Sichuan University, Chengdu, Sichuan Province (CN)

( * ) Notice: Subject to any disclaimer, the term of this patent is extended or adjusted under 35 U.S.C. 154(b) by 512 days.

(21) Appl. No.: 12/268,520

(22) Filed: Nov. 11, 2008

(65) Prior Publication Data

US 2009/0233370 A1 Sep. 17, 2009

(30) Foreign Application Priority Data

Mar. 11, 2008 (CN) .......................... 2008 1 0044937

(51) Int. Cl.
*G01N 35/00* (2006.01)
(52) U.S. Cl. ............ 436/43; 436/52; 436/120; 436/164; 422/68.1
(58) Field of Classification Search ........................ None
See application file for complete search history.

(56) References Cited

FOREIGN PATENT DOCUMENTS

CN 1560624 A * 1/2005

OTHER PUBLICATIONS

Liu S. et al. "Spectrophotometric Determination of Anionic Surfactants in Environmental Water Samples with Ethyl Violet," Journal of Southwest Teachers University 1989, 14, 54-57.*

Lavorante, A. F. "A multicommuted stop-flow system employing LEDs-based photometer for the sequential determination of anionic and cationic surfactants in water," Analytica Chimica Acta 2007, 600, 58-65; Published online Dec. 30, 2006.*
Wei L. et al. "Flow-injection Spectrophotometric Determination of Anionic Surfactants in Nature Water," Leather Science and Engineering, vol. 18, No. 3, 54-57, Jun. 2008.*
Moskvin, L. N. et al. "Flow-Injection Determination of Anionic Surfactants in Natural Waters in the Presence of Humic Acids," Journal of Analytical Chemistry, vol. 56, No. 8, 2001, pp. 763-766. Translated from Zhurnal Analiticheskoi Khimii, vol. 56, No. 8, 2001, pp. 856-859.*

* cited by examiner

*Primary Examiner* — Yelena G Gakh
*Assistant Examiner* — Michelle Adams
(74) *Attorney, Agent, or Firm* — Connolly Bove Lodge & Hutz LLP

(57) ABSTRACT

A method for assaying anionic detergents in seawater comprises: (1) flow a sample through a sample system and an analysis-detection system; flow a reference solution through a reference system, a valve, and the analysis-detection system; where the sample and reference are mixed; and flow the mixture into an optical cell to produce a baseline, (2) flow a sample through the sample system and analysis-detection system; flow a buffer through a buffer system and a color developing system; where the buffer and a color developer are mixed; and flow the resulting mixture through the valve and analysis-detection system; where the sample is mixed with the buffer and developer mixture; and flow the resulting mixture into the cell to produce the sample spectrogram, (3) repeat (1) and (2) with standards of known detergent concentrations for corresponding spectrograms, and (4) compare the sample spectrogram with the standard spectrograms to determine the sample detergent content.

12 Claims, 2 Drawing Sheets

METHOD FOR AUTOMATIC ASSAY OF ANIONIC DETERGENTS IN SEAWATER

FIELD OF THE INVENTION

This invention relates to a method for assay of anionic detergents (also known as anionic surfactants) in an environmental water body, and in particular, to a method for automatic assay of anionic detergents in seawater.

BACKGROUND OF THE INVENTION

As a pollutant to the environment, anionic detergents, after incorporated into a water body, accumulate on the surface of water and microparticles in the water, causing foaming or emulsification, which prevents oxygen from being incorporated into the water, and thereby leads to deterioration of water quality that jeopardizes organisms in the water.

According to the National Standard (GB17378.4—1998), the assay of anionic detergents in seawater is carried out by a spectrophotometric method using methylene blue, which is specified as follow: reacting an anionic-detergent-containing sample with methylene blue to yield a blue ion-pair compound, which is extracted into chloroform; measuring the absorbance of the extract at 650 nm, and expressing the assay result as the apparent concentration of sodium dodecylbenzene sulfonate. This method has the disadvantages of involving (1) time-consuming and complicated procedures due to the fact that each of the steps in the assay is carried out non-automatically, (2) the possibility of harming the working staff due to the toxicity of chloroform that is used as the solvent in the extraction step, and (3) a large consumption of chemicals.

SUMMARY OF THE INVENTION

An object of the present invention is to provide a method for automatic assay of anionic detergents in seawater to overcome the disadvantages of the method in the prior art. The present method not only meets the requirements for both sensitivity and accuracy of the assay of anionic detergents in seawater, but also is easier to carry out, faster in analyzing, and needs less chemicals.

The technical solution of the method for automatic assay of anionic detergents in seawater of the present invention is as follow:

(1) an analytic apparatus is provided with a flow system for buffer solution, a flow system for color developer solution, a flow system for reference solution, a flow system for samples, a sample valve, and a flow system for analysis and detection;

(2) the buffer solution ($R_1$) is an aqueous solution of potassium biphthalate-hydrochloric acid, the color developer solution ($R_2$) is an aqueous solution of ethyl violet-polyvinyl alcohol, and the reference solution ($R_{ref}$) is deionized water;

(3) a standard sample or a testing sample (S) flows along the flow system for samples and into the flow system for analysis and detection, and a reference solution ($R_{ref}$) flows along the flow system for reference solution, then through the sample valve, and into the flow system for analysis and detection, where the standard sample or the testing sample (S) is mixed with the reference solution ($R_{ref}$) and then flows into an optical flow cell so that a baseline is produced and mapped;

(4) a standard sample or a testing sample (S) flows along the flow system for samples and into the flow system for analysis and detection, and a buffer solution ($R_1$) flows along the flow system for buffer solution and into the flow system for color developer solution, where the buffer solution ($R_1$) is mixed with a color developer solution ($R_2$), the resulting mixture flows through the sample valve and into the flow system for analysis and detection, where the standard sample or the testing sample (S) is mixed with the mixture of the buffer solution ($R_1$) and the color developer solution ($R_2$) such that the color developer solution changes its color, then the resulting mixture flows into the optical flow cell so that a spectrogram is produced and mapped;

(5) comparing the spectrogram of the testing sample with the spectrograms of the standard samples, and then calculating the content of the anionic detergents in the testing sample.

In particular, the present invention provides a method for automatic assay of anionic detergents in seawater using an analytical apparatus comprising a flow system for buffer solution, a flow system for color developer solution, a flow system for reference solution, a flow system for samples, a sample valve and a flow system for analysis and detection, which method comprises the following steps:

(1) allowing a testing sample (S) to flow along the flow system for samples and into the flow system for analysis and detection, and allowing a reference solution ($R_{ref}$) to flow along the flow system for reference solution, then through the sample valve and into the flow system for analysis and detection, where the testing sample (S) is mixed with the reference solution ($R_{ref}$), and the resulting mixture then flows into an optical flow cell so that a baseline is produced and mapped;

(2) allowing a testing sample (S) to flow along the flow system for samples and into the flow system for analysis and detection, and allowing a buffer solution ($R_1$) to flow along the flow system for buffer solution and into the flow system for color developer solution, where the buffer solution ($R_1$) is mixed with a color developer solution ($R_2$), and the resulting mixture then flows through the sample valve and into the flow system for analysis and detection, where the testing sample (S) is mixed with the mixture of the buffer solution ($R_1$) and the color developer solution ($R_2$), and the resulting mixture then flows into an optical flow cell so that the spectrogram of the testing sample (S) is produced and mapped;

(3) repeating steps (1) and (2) with a series of standard samples having known concentrations of an anionic detergent instead of the testing sample (S) to obtain a series of spectrograms of the standard samples; and (4) comparing the spectrogram of the testing sample (S) with the series of spectrograms of the standard samples to determine the content of the anionic detergent in the testing sample (S);

wherein the buffer solution ($R_1$) is an aqueous solution of potassium biphthalate-hydrochloric acid, the color developer solution ($R_2$) is an aqueous solution of ethyl violet-polyvinyl alcohol, and the reference solution ($R_{ref}$) is deionized water.

Preferably, the buffer solution ($R_1$) and the color developer solution ($R_2$) in the method have the following compositions, respectively.

The buffer solution ($R_1$): potassium biphthalate at a concentration of 0.3 g/L~0.5 g/L, and hydrochloric acid at a concentration of $0.02 \times 10^{-2}$ mol/L~$0.20 \times 10^{-2}$ mol/L; and The color developer solution ($R_2$): ethyl violet at a concentration of $0.5 \times 10^{-2}$ g/L~$1.0 \times 10^{-2}$ μL, and polyvinyl alcohol at a concentration of 1.0 g/L~1.5 g/L.

Preferably, the optical flow cell has an optical path of 10 mm~30 mm, and the detection wavelength is 560 nm~570 nm in the method.

Preferably, the flow system for analysis and detection consists of a second mixer, a reactor and an optical flow cell which are sequentially connected in series.

The method of the present invention has the following beneficial effects:

(1) Ensuring both good sensitivity and good accuracy of the assay by reducing the differences in the assay results due to the difference in salinity (i.e. different concentrations of sodium chloride) of various seawater samples;
(2) Achieving online automatic assay of anionic detergents in seawater conveniently and quickly;
(3) Using less chemicals than the GB method, and the consumption of chemicals is only 1~2% of that in the GB method.

Figure 1:
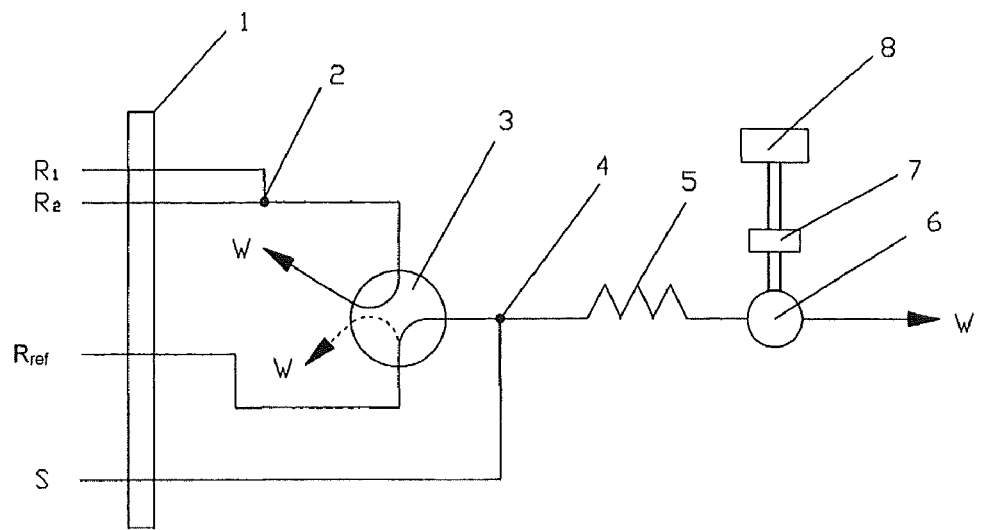
FIG. 1 is a schematic illustration of an analytical apparatus used in the method for automatic assay of anionic detergents in the seawater of the present invention, wherein the analytical apparatus is in its reference state.
Figure 2:
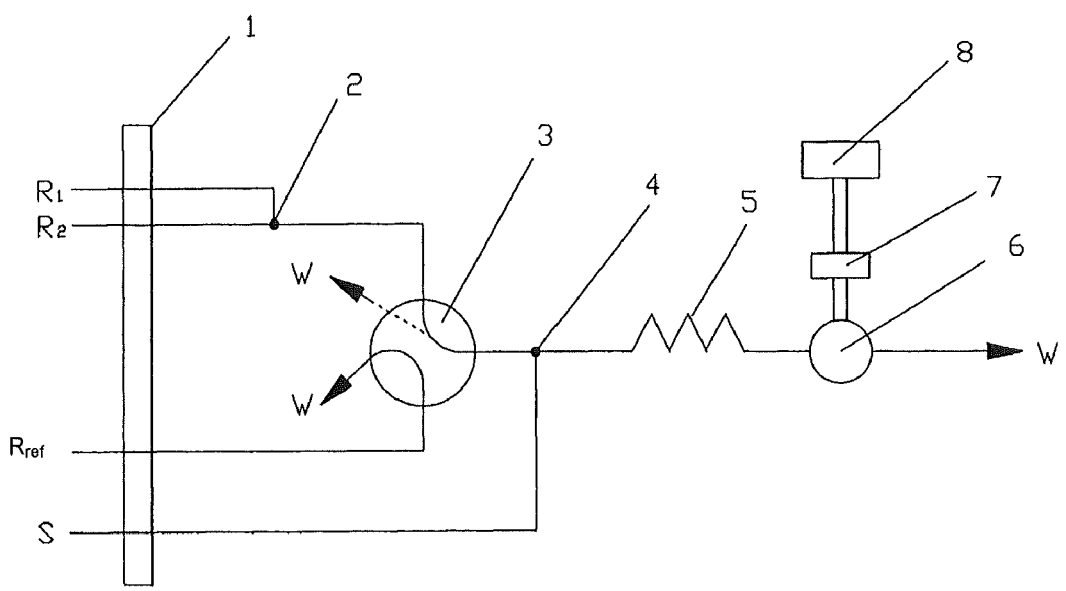
FIG. 2 is a schematic illustration of an analytical apparatus used in the method for automatic assay of anionic detergents in the seawater of the present invention, wherein the analytical apparatus is in its analyzing state.

The symbols in FIG. 1 and FIG. 2 have the following meanings: "1" stands for a low pressure pump, "2" stands for a first mixer, "3" stands for a sample valve, "4" stands for a second mixer, "5" stands for a reactor, "6" stands for an optical flow cell, "7" stands for an optical detector, "8" stands for a computer processing system, "S" refers to a standard sample or a testing sample, "$R_{ref}$" refers to a reference solution, "$R_1$" refers to a buffer solution, "$R_2$" refers to a color developer solution, and "W" refers to a waste liquid cell.

DETAILED DESCRIPTION OF THE INVENTION

The invention will be illustrated by way of examples below.

Example 1

In this example, the testing sample was seawater, and the analysis was conducted as specified below.

1. Preparation of the Standard Samples (1) 0.100 g sodium dodecylsulfate (SDS) was dissolved in 1000 mL deionized water to provide a mother liquor having a concentration of SDS of 100 mg/L;

(2) 0 mL, 0.050 mL, 0.100 mL, 0.200 mL, 0.300 mL and 0.400 mL of the mother liquor were respectively pipetted into a flask, and then each was diluted with blank seawater (i.e. seawater free of anionic detergents) to 50 mL such that a series of standard samples having respectively a concentration of SDS of 0 µg/L, 100 g/L, 200 µg/L, 400 µg/L, 600 µg/L and 800 µg/L were obtained.

2. Preparation of the Buffer Solution $R_1$

To a solution formed by dissolving 0.500 g potassium biphthalate in 1000 mL deionized water was added 0.033 mL hydrochloric acid (1:1) to provide the buffer solution $R_1$, which is an aqueous solution of potassium biphthalate (0.5 g/L) and hydrochloric acid ($0.02 \times 10^{-2}$ mol/L).

3. Preparation of the Color Developer Solution $R_2$ 0.500 g ethyl violet was dissolved in 1000 mL deionized water to provide an aqueous ethyl violet solution (0.5 g/L); and 10 g polyvinyl alcohol was dissolved in 1000 mL deionized water to provide an aqueous polyvinyl alcohol solution (10 g/L). The aqueous ethyl violet solution (20 mL, 0.5 g/L) and the aqueous polyvinyl alcohol solution (150 mL, 10 g/L) were mixed and then diluted with deionized water to 1000 mL to provide the color developer solution $R_2$, which is an aqueous solution of ethyl violet ($1.0 \times 10^{-2}$ g/L) and polyvinyl alcohol (1.5 g/L).

The chemicals used in the preparation of the standard samples, the buffer solution $R_1$ and the color developer solution $R_2$ were analytical pure.

4. Reference Solution $R_{ref}$

Deionized water was used as the reference solution $R_{ref}$.

5. Mapping of the Spectrogram of the Testing Sample

Figure 3:
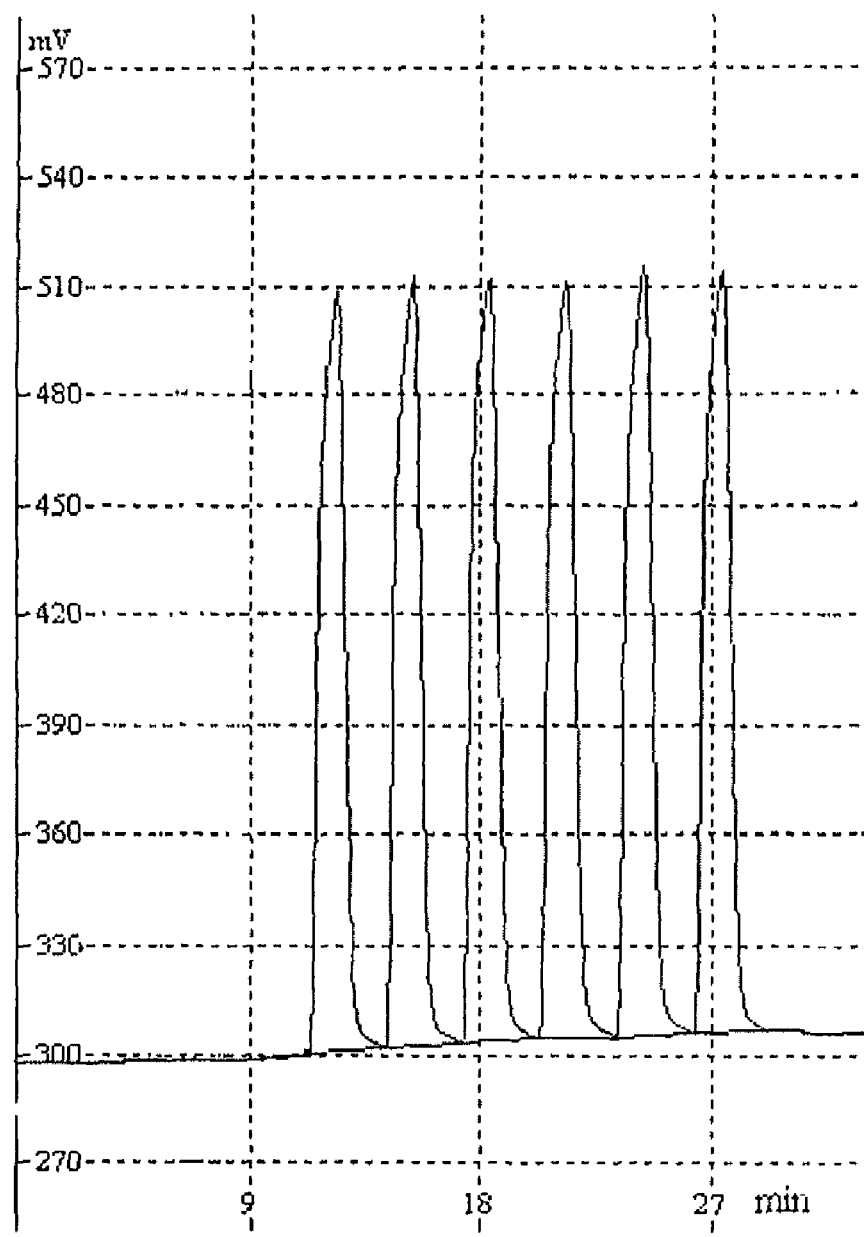
FIG. 3 is the spectrogram of the seawater sample tested in Example 1.

The assay was carried out using the automatic analytical apparatus as shown in FIG. 1. The low pressure pump 1 of the apparatus was a four-channel constant flow pump, of which the pump capacity was 0.2 ml/min~1.0 ml/min and the working pressure was $2 \times 10^5$ Pa~$3 \times 10^5$ Pa. The optical path of the optical flow cell 6 was 20 mm, and the detection wavelength was 560 nm. Both the first mixer 2 and the second mixer 4 were of a three-channel structure. The reactor 5 was of a coil structure and a length of 3 m, which was made by winding a polytetrafluoroethylene tube having an inner diameter of 0.5 mm. The base line was mapped first while the apparatus was in its reference state, as shown in FIG. 1. The apparatus was turned on. Driven by the low pressure pump 1, the testing sample S flowed along the flow system for samples and into the flow system for analysis and detection, while the reference solution $R_{ref}$ flowed along the flow system for reference solution, then through the sample valve 3, and into the flow system for analysis and detection. After the testing sample S was mixed with the reference solution $R_{ref}$ in the second mixer 4 and the reactor 5 of the flow system for analysis and detection, the resulting mixture flowed into the optical flow cell 6. Signals were transmitted from the optical detector 7 to the computer processing system 8 so that the base line was displayed on the computer display. The sample valve 3 was converted to its analytical state after the base line was mapped, as shown in FIG. 2. Driven by the low pressure pump 1, the testing sample S flowed along the flow system for samples and into the flow system for analysis and detection, while the buffer solution $R_1$ flowed along the flow system for buffer solution and into the flow system for color developer solution, where the buffer solution $R_1$ was mixed with the color developer solution $R_2$, and the resulting mixture then flowed through the sample valve 3 and into the flow system for analysis and detection. In the flow system for analysis and detection, the testing sample S was mixed with the mixture of the buffer solution $R_1$ and the color developer solution $R_2$ in the second mixer 4 and the reactor 5, where an association reaction occurred to give ion pairs, resulting in the color change of the color developer solution. Then the resulting mixture flowed into the optical flow cell 6, and signals were transmitted from the optical detector 7 to the computer processing system 8 so that the spectrogram of the anionic detergent in the testing sample was displayed on the computer display, as shown in FIG. 3.

6. Mapping of the Spectrograms of the Standard Samples

The apparatus, the buffer solution $R_1$, the color developer solution $R_2$, and the reference solution $R_{ref}$ used for mapping the spectrograms of the standard samples were the same as those used for mapping the spectrogram of the testing sample, and the assay procedure was also the same. A series of spectrograms were obtained by testing each of the standard samples in the sequence of from the sample of the lowest concentration to that of the highest concentration.

7. Calculation and the Result of the Assay

The spectrogram of the testing sample was compared with those of the standard samples, and the content of the anionic detergent in the testing sample was determined. The calculation and the result are as shown below.

TABLE 1

The concentrations of the standard samples and the peak heights in the spectrograms

| Concentrations of the standard samples (μg/L) | 0 | 100 | 200 | 400 |
|---|---|---|---|---|
| Peak heights in the spectrograms (mV) | 219.2 | 206.9 | 195.6 | 172.5 |

A linear equation was derived from the data as shown in Table 1:

$$y=-0.1163x+218.9$$

wherein "y" represented the peak height in the spectrogram, and "x" represented the content (concentration) of the anionic detergent.

The peak height in the spectrogram of the testing sample of seawater was 209.5 mV (see FIG. 3). By calculating with the above linear equation, the content of the anionic detergent in the testing sample was determined to be 80.83 μg/L.

Example 2

In this example, the testing sample was seawater, and the analysis was conducted as specified below.

1. Preparation of the Standard Samples (1) 0.100 g sodium dodecylsulfate (SDS) was dissolved in 1000 mL deionized water to provide a mother liquor having a concentration of SDS of 100 mg/L;

(2) 0 mL, 0.050 mL, 0.100 mL, 0.200 mL, 0.300 mL and 0.400 mL of the mother liquor were respectively pipetted into a flask, and then each was diluted with blank seawater (i.e. seawater free of anionic detergents) to 50 mL such that a series of standard samples having respectively a concentration of SDS of 0 μg/L, 100 μg/L, 200 μg/L, 400 μg/L, 600 μg/L and 800 μg/L were obtained.

2. Preparation of the Buffer Solution $R_1$

To a solution formed by dissolving 0.300 g potassium biphthalate in 1000 mL deionized water was added 0.33 mL hydrochloric acid (1:1) to provide the buffer solution $R_1$, which is an aqueous solution of potassium biphthalate (0.3 g/L) and hydrochloric acid ($0.20 \times 10^{-2}$ mol/L).

3. Preparation of the Color Developer Solution $R_2$ 0.500 g ethyl violet was dissolved in 1000 mL deionized water to provide an aqueous ethyl violet solution (0.5 g/L); and 10 g polyvinyl alcohol was dissolved in 1000 mL deionized water to provide an aqueous polyvinyl alcohol solution (10 g/L). The aqueous ethyl violet solution (10 mL, 0.5 g/L) and the aqueous polyvinyl alcohol solution (100 mL, 10 g/L) were mixed and then diluted with deionized water to 1000 mL to provide the color developer solution $R_2$, which is an aqueous solution of ethyl violet ($0.5 \times 10^{-2}$ g/L) and polyvinyl alcohol (1.0 g/L).

The chemicals used in the preparation of the standard samples, the buffer solution $R_1$ and the color developer solution $R_2$ were analytical pure.

4. Reference Solution $R_{Ref}$

Deionized water was used as the reference solution $R_{ref}$.

5. Mapping of the Spectrogram of the Testing Sample

The assay was carried out using the automatic analytical apparatus as shown in FIG. 1. The low pressure pump 1 of the apparatus was a four-channel constant flow pump, of which the pump capacity was 0.2 ml/min~1.0 ml/min and the working pressure was $2 \times 10^5$ Pa~$3 \times 10^5$ Pa. The optical path of the optical flow cell 6 was 30 mm, and the detection wavelength was 570 mm. Both the first mixer 2 and the second mixer 4 were of a three-channel structure. The reactor 5 was of a coil structure and a length of 3 m, which was made by winding a polytetrafluoroethylene tube having an inner diameter of 0.5 mm. The base line was mapped first while the apparatus was in its reference state, as shown in FIG. 1. The apparatus was turned on. Driven by the low pressure pump 1, the testing sample S flowed along the flow system for samples and into the flow system for analysis and detection, while the reference solution $R_{ref}$ flowed along the flow system for reference solution, then through the sample valve 3, and into the flow system for analysis and detection. After the testing sample S was mixed with the reference solution $R_{ref}$ in the second mixer 4 and the reactor 5 of the flow system for analysis and detection, the resulting mixture flowed into the optical flow cell 6. Signals were transmitted from the optical detector 7 to the computer processing system 8 so that the base line was displayed on the computer display. The sample valve 3 was converted to its analytical state after the base line was mapped, as shown in FIG. 2. Driven by the low pressure pump 1, the testing sample S flowed along the flow system for samples and into the flow system for analysis and detection, while the buffer solution $R_1$ flowed along the flow system for buffer solution and into the flow system for color developer solution, where the buffer solution $R_1$ was mixed with the color developer solution $R_2$, and the resulting mixture then flowed through the sample valve 3 and into the flow system for analysis and detection. In the flow system for analysis and detection, the testing sample S was mixed with the mixture of the buffer solution $R_1$ and the color developer solution $R_2$ in the second mixer 4 and the reactor 5, where an association reaction occurred to give ion pairs, resulting in the color change of the color developer solution. Then the resulting mixture flowed into the optical flow cell 6, and signals were transmitted from the optical detector 7 to the computer processing system 8 so that the spectrogram of the anionic detergent in the testing sample was displayed on the computer display.

6. Mapping of the Spectrograms of the Standard Samples

The apparatus, the buffer solution $R_1$, the color developer solution $R_2$, and the reference solution $R_{ref}$ used for mapping the spectrograms of the standard samples were the same as those used for mapping the spectrogram of the testing sample, and the assay procedure was also the same. A series of spectrograms were obtained by testing each of the standard samples in the sequence of from the sample of the lowest concentration to that of the highest concentration.

7. Calculation and the Result of the Assay

The spectrogram of the testing sample was compared with those of the standard samples, and the content of the anionic detergent in the testing sample was determined. The calculation and the result are as shown below.

TABLE 2

The concentrations of the standard samples and the peak heights in the spectrograms

| Concentrations of the standard samples (μg/L) | 0 | 100 | 200 | 400 |
|---|---|---|---|---|

TABLE 2-continued

| The concentrations of the standard samples and the peak heights in the spectrograms | | | | |
|---|---|---|---|---|
| Peak heights in the spectrograms (mV) | 283.3 | 268.7 | 253.3 | 221.6 |

A linear equation was derived from the data as shown in Table 2:

$$y=-0.1547x+283.8$$

wherein "y" represented the peak height in the spectrogram, and "x" represented the content (concentration) of the anionic detergent.

The peak height in the spectrogram of the testing sample of seawater was 276.2 mV. By calculating with the above linear equation, the content of the anionic detergent in the testing sample was determined to be 49.13 μg/L.

What is claimed is:

1. A method for automatic assay of anionic detergents in seawater using an analytical apparatus comprising a flow system for buffer solution, a flow system for color developer solution, a flow system for reference solution, a flow system for samples, a sample valve and a flow system for analysis and detection, wherein the method comprises the following steps:
    (1) allowing a testing sample (S) to flow along the flow system for samples and into the flow system for analysis and detection, and allowing a reference solution ($R_{ref}$) to flow along the flow system for reference solution, then through the sample valve and into the flow system for analysis and detection where the testing sample (S) is mixed with the reference solution ($R_{ref}$) to form a first mixture of the testing sample (S) and the reference solution ($R_{ref}$), and allowing the first mixture to then flow into an optical flow cell so that a baseline is produced and mapped;
    (2) allowing the testing sample (S) to flow along the flow system for samples and into the flow system for analysis and detection, and allowing a buffer solution ($R_1$) to flow along the flow system for buffer solution and into the flow system for color developer solution where the buffer solution ($R_1$) is mixed with a color developer solution ($R_2$) to form a second mixture of the buffer solution ($R_1$) and the color developer solution ($R_2$), and allowing the second mixture to then flow through the sample valve and into the flow system for analysis and detection where the testing sample (S) is mixed with the second mixture to form a third mixture of the testing sample (S), the buffer solution ($R_1$) and the color developer solution ($R_2$), and allowing the third mixture to then flow into an optical flow cell so that a spectrogram of the testing sample (S) is produced and mapped;
    (3) repeating steps (1) and (2) with a series of standard samples having known concentrations of an anionic detergent instead of the testing sample (S) to obtain a series of spectrograms of the standard samples; and
    (4) comparing the spectrogram of the testing sample (S) with the series of spectrograms of the standard samples to determine the content of the anionic detergents in the testing sample (S);

wherein the testing sample (S) is seawater, the buffer solution ($R_1$) is an aqueous solution of potassium biphthalate-hydrochloric acid, the color developer solution ($R_2$) is an aqueous solution of ethyl violet-polyvinyl alcohol, and the reference solution ($R_{ref}$) is deionized water.

2. The method for automatic assay of anionic detergents in seawater of claim 1 wherein the concentration of potassium biphthalate in the buffer solution ($R_1$) is from about 0.3 g/L to about 0.5 g/L, and the concentration of hydrochloric acid in the buffer solution ($R_1$) is from about $0.02 \times 10^{-2}$ mol/L to about $0.20 \times 10^{-2}$ mol/L.

3. The method for automatic assay of anionic detergents in seawater of claim 1 wherein the concentration of ethyl violet in the color developer solution ($R_2$) is from about $0.5 \times 10^{-2}$ g/L to about $1.0 \times 10^{-2}$ g/L, and the concentration of polyvinyl alcohol in the color developer solution ($R_2$) is from about 1.0 g/L to about 1.5 g/L.

4. The method for automatic assay of anionic detergents in seawater of claim 1 wherein the optical flow cell has an optical path of from about 10 mm to about 30 mm, and the detection wavelength is from about 560 to about 570 nm.

5. The method for automatic assay of anionic detergents in seawater of claim 3 wherein the optical flow cell has an optical path of from about 10 mm to about 30 mm, and the detection wavelength is from about 560 to about 570 nm.

6. The method for automatic assay of anionic detergents in seawater of claim 1 wherein the flow system for analysis and detection consists of a mixer (4), a reactor (5) and an optical flow cell (6) that are sequentially connected in series.

7. The method for automatic assay of anionic detergents in seawater of claim 3 wherein the flow system for analysis and detection consists of a mixer (4), a reactor (5) and an optical flow cell (6) that are sequentially connected in series.

8. The method for automatic assay of anionic detergents in seawater of claim 4 wherein the flow system for analysis and detection consists of a mixer (4), a reactor (5) and an optical flow cell (6) that are sequentially connected in series.

9. The method for automatic assay of anionic detergents in seawater of claim 5 wherein the flow system for analysis and detection consists of a mixer (4), a reactor (5) and an optical flow cell (6) that are sequentially connected in series.

10. The method for automatic assay of anionic detergents in seawater of claim 2 wherein the concentration of ethyl violet in the color developer solution ($R_2$) is from about $0.5 \times 10^{-2}$ g/L to about $1.0 \times 10^{-2}$ g/L, and the concentration of polyvinyl alcohol in the color developer solution ($R_2$) is from about 1.0 g/L to about 1.5 g/L.

11. The method for automatic assay of anionic detergents in seawater of claim 2 wherein the optical flow cell has an optical path of from about 10 mm to about 30 mm, and the detection wavelength is from about 560 to about 570 nm.

12. The method for automatic assay of anionic detergents in seawater of claim 2 wherein the flow system for analysis and detection consists of a mixer (4), a reactor (5) and an optical flow cell (6) that are sequentially connected in series.

* * * * *